United States Patent
Haibach

(10) Patent No.: US 10,016,572 B2
(45) Date of Patent: Jul. 10, 2018

(54) PIVOTING QUICK RELEASE FOR A PATIENT INTERFACE DEVICE

(71) Applicant: KONINKLIJKE PHILIPS N.V., Eindhoven (NL)

(72) Inventor: Richard Thomas Haibach, Verona, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 577 days.

(21) Appl. No.: 14/418,121

(22) PCT Filed: Jul. 24, 2013

(86) PCT No.: PCT/IB2013/056063
§ 371 (c)(1),
(2) Date: Jan. 29, 2015

(87) PCT Pub. No.: WO2014/020494
PCT Pub. Date: Feb. 6, 2014

(65) Prior Publication Data
US 2015/0165149 A1     Jun. 18, 2015

Related U.S. Application Data

(60) Provisional application No. 61/678,169, filed on Aug. 1, 2012.

(51) Int. Cl.
*A61M 16/06*     (2006.01)

(52) U.S. Cl.
CPC .......... *A61M 16/065* (2014.02); *A61M 16/06* (2013.01); *A61M 16/0633* (2014.02); *A61M 16/0683* (2013.01); *A61M 16/0616* (2014.02)

(58) Field of Classification Search
CPC .......... A61M 16/0605; A61M 16/0611; A61M 16/0633; A61M 16/0638; A61M 16/0644;
(Continued)

(56) References Cited

U.S. PATENT DOCUMENTS

| | | |
|---|---|---|
| 2,444,417 A | 7/1948 | Bierman |
| 2,942,072 A | 6/1960 | Cunningham |

(Continued)

FOREIGN PATENT DOCUMENTS

| | | |
|---|---|---|
| WO | 2003033077 A1 | 4/2003 |
| WO | 2003035156 A2 | 5/2003 |

(Continued)

*Primary Examiner* — Rachel T Sippel
(74) *Attorney, Agent, or Firm* — Michael W. Haas

(57) ABSTRACT

A pivotable frame assembly (60) for a patient interface device (8) is provided. The patient interface device includes a mask (10) and a support assembly (40). The support assembly includes a first support member (52), a first strap (42A) and a second strap (42B), the first strap coupled at two locations to the first support member. The second strap is structured to be temporarily coupled to a mask first, temporary support assembly coupling (18). The pivotable frame assembly includes a frame member (62), a hinge assembly (64) and a support assembly strap coupling (66). The hinge assembly pivotally coupled the frame assembly and the mask. In this configuration, when the mask is coupled to the hinge assembly second component (82), the mask may move between a first position, wherein the mask is pivoted away from the user's face, and a second position, wherein the mask is sealed against the user's face.

19 Claims, 4 Drawing Sheets

(58) Field of Classification Search
CPC ............ A61M 16/065; A61M 16/0683; A61M 16/0688; A61M 16/0694; A61M 2016/0661; A62B 18/086; A62B 7/00–7/14; A62B 9/025; A62B 17/001
USPC .................................................... 128/202.15
See application file for complete search history.

(56) References Cited

U.S. PATENT DOCUMENTS

| | | | |
|---|---|---|---|
| 6,338,342 B1 | 1/2002 | Fecteau | |
| 2002/0078953 A1 | 6/2002 | Fecteau | |
| 2005/0211252 A1 | 9/2005 | Lang | |
| 2007/0215161 A1* | 9/2007 | Frater | A61M 16/06 128/206.24 |
| 2009/0173343 A1* | 7/2009 | Omura | A44B 11/2519 128/202.27 |
| 2010/0018534 A1* | 1/2010 | Veliss | A61M 16/06 128/206.24 |
| 2010/0108069 A1* | 5/2010 | Chang | A61M 16/06 128/205.25 |
| 2010/0252037 A1* | 10/2010 | Wondka | A61M 16/0666 128/203.12 |
| 2012/0111333 A1* | 5/2012 | Eifler | A61M 16/0683 128/205.25 |

FOREIGN PATENT DOCUMENTS

| | | |
|---|---|---|
| WO | 2004021960 A2 | 3/2004 |
| WO | 2009125348 A1 | 10/2009 |
| WO | 2010073139 A1 | 7/2010 |
| WO | 2011110968 A2 | 9/2011 |

* cited by examiner

PIVOTING QUICK RELEASE FOR A PATIENT INTERFACE DEVICE

CROSS-REFERENCE TO PRIOR APPLICATIONS

This application claims the priority benefit under 35 U.S.C. § 371 of International Patent Application No. PCT/IB2013/056063, filed on Jul. 24, 2013, which claims the priority benefit of U.S. Provisional Patent Application No. 61/678,169, filed on Aug. 1, 2012, the contents of which are herein incorporated by reference.

BACKGROUND OF THE INVENTION

1. Field of the Invention

The present invention relates to patient interface devices for transporting a gas to and/or from an airway of a user which include, but not limited to, a frame assembly in an patient interface device that is structured to pivotally support a mask so that the mask may move between a first position, wherein the mask is pivoted away from the user's face, and a second position, wherein the mask is sealed against the user's face.

2. Description of the Related Art

Masks used as patient interface devices may include a relatively rigid faceplate and a softer patient contacting cushion. Alternatively, a flexible faceplate may act as a patient contacting cushion. Hereinafter, this description shall refer to a patient contacting cushion, but it is understood that the patient contacting cushion may be a flexible faceplate as well. The patient contacting cushion is made from a relatively soft material that is structured to substantially adapt to the contour of the user's face. Thus, the patient contacting cushion creates a generally continuous seal about the user's nose and/or mouth.

Masks are supported on the user by a support assembly. The support assembly may include a generally rigid frame assembly and/or a strap assembly. The straps may be elastic or non-elastic. The straps may have an adjustable length. As is known, a support assembly comprised exclusively of straps may bias, i.e. pull, the mask too tightly against the user's face. Thus, a frame assembly may be used to properly position the mask relative to the user's face. The frame assembly is coupled to the strap assembly. To use the patient interface device, a user typically positions the frame assembly and mask in front of their face, then places the strap assembly over or around their head. The user then tightens the strap assembly, if needed, thereby maintaining the mask in place of the user's nose and/or mouth.

There are several disadvantages to this configuration. One disadvantage is that the mask is held firmly in place when a user wishes to remove the mask. That is, when a user is taking off the mask, the user must loosen multiple straps or disconnect multiple couplings. For users with limited dexterity, these operations may be especially difficult. Further, if the user desires to remove the mask temporarily, e.g. to speak, the user must loosen the strap assembly, substantially remove the mask from in front of the user's face and then reinstall the mask when needed. Another disadvantage is that the user may end up adjusting the straps resulting in an uncomfortable fit. That is, users may find a particular configuration of the straps is more comfortable than any other configuration of the straps. The user, typically, would like to keep the strap assembly in such a configuration but is forced to move the straps out of the comfortable configuration when loosening the support assembly or removing the mask. The user may then have difficulty finding the comfortable configuration again. Further, the act of adjusting multiple straps is time consuming and may be difficult for users with limited dexterity.

There is, therefore, a desire to have a support assembly that allows a user to quickly and easily reposition a mask temporarily. There is a further desire for a support assembly that may be substantially maintained in a selected configuration while allowing the user to remove and reinstall the mask.

SUMMARY OF THE INVENTION

It is an object of this invention to provide a pivotable frame assembly for a patient interface device. The patient interface device includes a mask and a support assembly. The mask has a first, temporary support assembly coupling. The support assembly includes a first support member, a first strap and a second strap; the first strap coupled at two locations to the first support member. The second strap is structured to be temporarily coupled to the mask first, temporary support assembly coupling. The pivotable frame assembly includes a frame member, a hinge assembly and a support assembly strap coupling. The frame member is coupled to the support assembly first support member. The hinge assembly has a first component and a second component, the hinge assembly first and second components being pivotally coupled to each other. The hinge assembly first component is coupled to the frame member. The hinge assembly second component is structured to be coupled to the mask. In this configuration, when the mask is coupled to the hinge assembly second component, the mask may move between a first position, wherein the mask is pivoted away from the user's face, and a second position, wherein the mask is sealed against the user's face.

It is a further object of this invention to provide a patient interface device including a mask and a support assembly. The mask has a first, temporary support assembly coupling. The support assembly has a pivotable frame assembly, a frame assembly, and a strap assembly. The strap assembly having at least one strap, the at least one strap having four couplings. The frame assembly having a first support member structured to be coupled to a user's face. The pivotable frame assembly including a frame member, a hinge assembly and a support assembly strap coupling. The pivotable frame assembly frame member coupled to the frame assembly first support member. The hinge assembly having a first component and a second component. The hinge assembly first and second components being pivotally coupled to each other. The hinge assembly first component coupled to the pivotable frame assembly frame member. The hinge assembly second component coupled to the mask. In this configuration, the mask may move between a first position, wherein the mask is pivoted away from the user's face, and a second position, wherein the mask is sealed against the user's face.

It is a further object of this invention to provide a method of using the patient interface device that includes the steps of donning the patient interface device with the mask in the second position, temporarily coupling a strap to the mask strap coupling, temporarily decoupling a strap to the mask strap coupling, moving the mask to the first position, moving the mask to the second position, and, temporarily re-coupling a strap to the mask strap coupling.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

Figure 1:
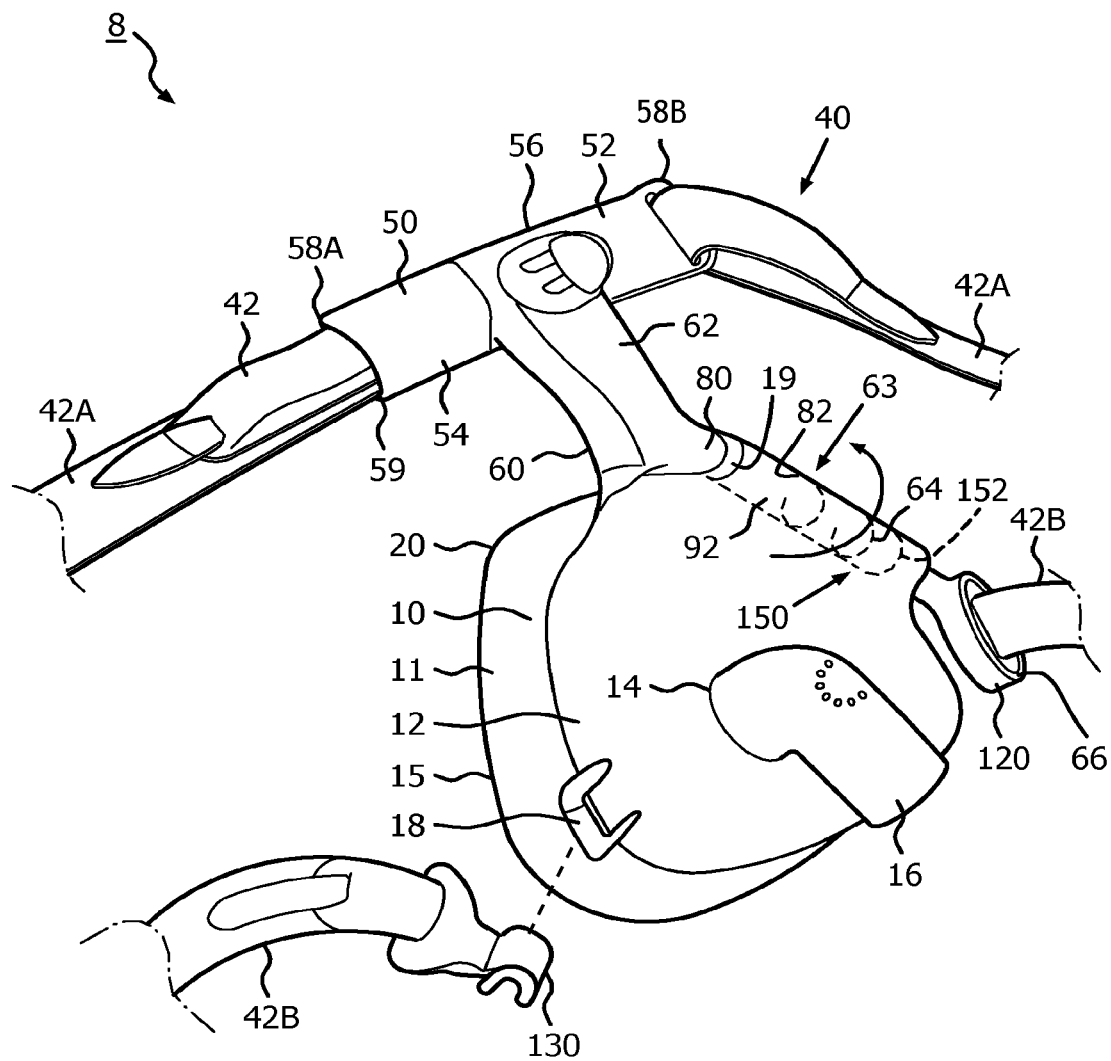
FIG. 1 is an isometric view of a patient interface device.

As used herein, the singular form of "a," "an," and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

As used herein, "a generally continuous seal" may have a gap or may gap when the user moves. As used herein, "a more complete seal" has a gap that is shorter in length than a gap of a generally continuous seal, or, is resistant to gapping when the user moves.

As used herein, "correspond" indicates that two structural components are sized to engage each other with a minimum amount of friction. Thus, an opening which corresponds to a member is sized slightly larger than the member so that the member may pass through the opening with a minimum amount of friction. This definition is modified if the two components are said to fit "snugly" together. In that situation, the difference between the size of the components is even smaller whereby the amount of friction increases.

As used herein, a "coupling component" is one element of a coupling assembly. That is, a coupling assembly includes at least two elements, or components, that are structured to be coupled together. It is understood that the elements of a coupling assembly correspond to each other or are otherwise structured to be joined together. For example, in a coupling assembly, if one coupling element is a bolt, the other coupling element is a nut. Further, it is understood that the two elements of a coupling assembly may not be described at the same time.

FIG. 1 shows a patient interface device 8 according to an exemplary embodiment of the invention. Patient interface device 8 includes a respiratory mask 10 and a support assembly 40. Mask 10 is coupled to a pressure generating system (not shown) via a patient circuit, as is conventionally known in the art. For purposes of the present invention, the pressure generating system is any device capable of generating a flow of breathing gas or providing gas at an elevated pressure. Examples of such pressure generating systems include a ventilator, CPAP device, or variable pressure device, e.g. an auto-titrating device, proportional assist ventilation (PAV®) device, proportional positive airway pressure (PPAP) device, C-Flex™ device, Bi-Flex® device, or a BiPAP® device manufactured and distributed by Philips Respironics of Murrysville, Pa., in which the pressure provided to the patient varies with the patient's respiratory cycle so that a higher pressure is delivered during inspiration than during expiration, or other pressure support device.

In the exemplary illustrated embodiment, respiratory mask 10 includes a body 11 with a faceplate 12 and a cushion 15, discussed below. In an exemplary embodiment, faceplate 12 is substantially rigid. In an exemplary embodiment, shown in FIG. 1, faceplate 12 is a single piece structured to cover the user's nose. That is, mask 10 has a peripheral contour that is structured to extend over a user's nose and mouth. In this embodiment, body 11 is coextensive with faceplate 12. It is understood that this is an exemplary embodiment and mask 10 may be structured to extend over the user's nose and mouth, or, just the user's mouth. Further, it is understood that the faceplate 12 may be made from a soft or flexible material. Faceplate 12 defines lower opening 14. Lower opening 14 can function as a gas inlet. Gas inlet 14 (lower opening 14) can be coupled to a coupling device 16, such as a swivel conduit, for carrying gas such as air between mask 10 and an external gas source (not shown), such as a blower, or any other suitable device.

It is to be further understood that the term "mask" is used to describe any structure that seals over an airway of a user. In the illustrated embodiment, this is a nasal mask that seals around the nares of the user. However, the present invention contemplates that the term mask also covers nasal cushions that seal only around the bottom of the nose, as well as nasal prongs that seal around each nare, and may insert, at least partially, into the nares of the user.

It is contemplated that the external gas source can encompass, without limitation, any gas delivery or gas generation system capable of supplying gas for consumption by a user. Non-limiting examples of various gas delivery therapies can include but are not limited to continuous positive airway pressure (CPAP) therapy, auto-titration positive airway pressure therapy, and bi-level positive airway pressure (BiPAP) therapy, as noted above. The particular coupling device 16, shown in FIG. 1, is not meant to be limiting and it should be understood that the present invention contemplates a variety of different coupling devices that could be attached, either permanently or selectively, to lower opening 14 to carry gas to or from mask 10. Thus, a variety of coupling devices (e.g., with or without swivels on one or both ends, and with or without an exhalation system formed integral to the device) may be substituted for coupling device 16. Coupling device 16 may also include other features, such as exhaust ports, filters, coupling ports, gas monitoring windows, valves, and other such features found on conventional patient circuits.

Mask 10 further includes a first, temporary, strap coupling 18 and a second, hinge assembly coupling 19. Mask first strap coupling 18 is a "temporary coupling." As used herein, a "temporary coupling" is a coupling that may be easily coupled and decoupled. Couplings such as, but not limited to, snaps, hooks, and clips are "temporary couplings." A "temporary coupling" is structured to "temporarily couple" two elements. Alternatively, a coupling may be a "semi-permanent coupling." As used herein, "semi-permanent coupling" means that the components of the coupling, such as, but not limited to a strap 42, may be coupled to another element and cannot be easily decoupled therefrom. That is, the elements would typically be decoupled for a specific purpose, e.g. cleaning forehead pad 54, rather than a general operation, such as donning or removing mask 10. Loop couplings, e.g. loops of strap 42 passed through a slot, are examples of "semi-permanent couplings." A "semi-permanent coupling" is structured to "semi-permanently couple" two elements.

Mask second, hinge assembly coupling 19 is structured to pivotally couple mask 10 to support assembly 40. Mask second, hinge assembly coupling 19 may be part of hinge assembly 64, described below. For example, in one exemplary embodiment, shown in FIG. 1, if hinge assembly 64 is a barrel hinge 63, mask second, pivotal, support assembly coupling 19 may be an elongated loop 92 through which a hinge assembly pin 90 extends, as described below. In an alternate exemplary embodiment, shown in FIG. 2, mask second, hinge assembly coupling 19 is a mounting 84, to which a living hinge 89 component may be coupled or fixed.

Cushion 15 is structured to extend from faceplate 12 toward the user's face and generally defines the depth of mask 10. Cushion 15 includes a cushion body 20 made from a flexible material. Cushion 15 is structured to engage the user's face and provide a generally continuous seal. This seal may be improved to be a more complete seal if mask 10 is maintained in an orientation that is generally tangent relative to the user's face. The bias that causes cushion 15 to engage the user's face is created by support assembly 40.

The present invention contemplates that cushion 15 can be any suitable seal having any size, shape, and geometry, and can be formed from any material, or combination of materials that accomplishes this function. For example, cushion 15 can be a one or two-flap silicon structure, or it can include gel materials. Moreover, cushion 15 can be formed as a customized element or include customizable features, such as inflatable bladders. In short, the cushion can be anything that accomplishes the sealing function.

Support assembly 40 includes a strap 42, as shown, an upper strap 42A and a lower strap 42B, a frame assembly 50, and a pivotable frame assembly 60. Straps 42 may be made from an elastic or non-elastic material. Straps 42 are structured to be coupled, directly or indirectly, to mask 10. Straps 42, therefore have a "mask coupling" disposed thereon, generally near an end of a strap 42. As used herein, a "mask coupling" may not be a direct coupling to mask 10. That is, if a member of frame assembly 50 is coupled to mask 10, then the coupling between strap 42 and that member of frame assembly 50 is a "mask coupling." Conversely, the coupling components on frame assembly 50 and mask 10 that are coupled to a "mask coupling" are identified as a "strap coupling," as discussed below. In an alternate exemplary embodiment, the strap 42 may be a web, including a unitary web, (not shown) having multiple elements and multiple mask couplings. In the disclosed exemplary embodiment, each strap 42 is structured to extend about the user's head.

Frame assembly 50 includes at least a first support member 52 structured to be coupled to a user's face. First support member 52 is structured to provide a relatively stationary mounting for pivotable frame assembly 60. As shown, first support member 52 is a forehead pad 54 including an elongated body 56 structured to extend laterally across the user's forehead. Forehead pad 54 includes two strap couplings 58A, 58B, each disposed at one lateral end of forehead pad elongated body 56. Forehead pad strap couplings 58A, 58B are slots 59 in forehead pad elongated body 56. The ends of strap 42 may be passed through and looped about forehead pad strap couplings 58A, 58B. Forehead pad 54 may include padded elements (not shown) disposed on an inner side of forehead pad elongated body 56 which are structured to contact the user. Alternatively, forehead pad elongated body 56 may contact the user.

Upper strap 42A is coupled to both forehead pad strap couplings 58A, 58B. That is, each end of upper strap 42A is coupled to one forehead pad strap couplings 58A, 58B. In this configuration, upper strap 42A may extend about the user's head at an elevation generally above the user's ears. It is noted that at an elevation above a user's ears, a head, typically has a reducing circumference. That is, the cross-sectional area of a user's head becomes smaller at higher elevations above the ear. Thus, upper strap 42A can be adjusted to a desired maximum length which does not have to be extended to remove upper strap 42A. That is, as the user's head becomes more narrow at higher elevations, upper strap 42A will have a sufficient length to allow upper strap 42A to be moved over the user's head without further adjustment. Thus, in this configuration, upper strap 42A may be adjusted to a selected length and generally remain at the selected length. Accordingly, forehead pad strap couplings 58A, 58B are semi-permanently coupled to upper strap 42A.

Pivotable frame assembly 60 includes a frame member 62, a hinge assembly 64 and a strap coupling 66. Pivotable frame assembly frame member 62 is structured to be, and is, coupled to first support member 52, i.e. forehead pad 54. In an exemplary embodiment, pivotable frame assembly frame member 62 is fixed to first support member 52, i.e. forehead pad 54. In one exemplary embodiment, shown in FIG. 3, pivotable frame assembly frame member 62 is an elongated vertical frame member 70 structured to extend generally vertically downward from first support member 52 at a location disposed over the user's nose when support assembly 40 is in use. In an alternate exemplary embodiment, shown in FIG. 4, pivotable frame assembly frame member 62 has an elongated horizontal member 76, structured to extend generally horizontally under the user's eye when support assembly 40 is in use. Pivotable frame assembly frame member 62 is structured to provide support for pivotable frame assembly hinge assembly 64.

Figure 2:
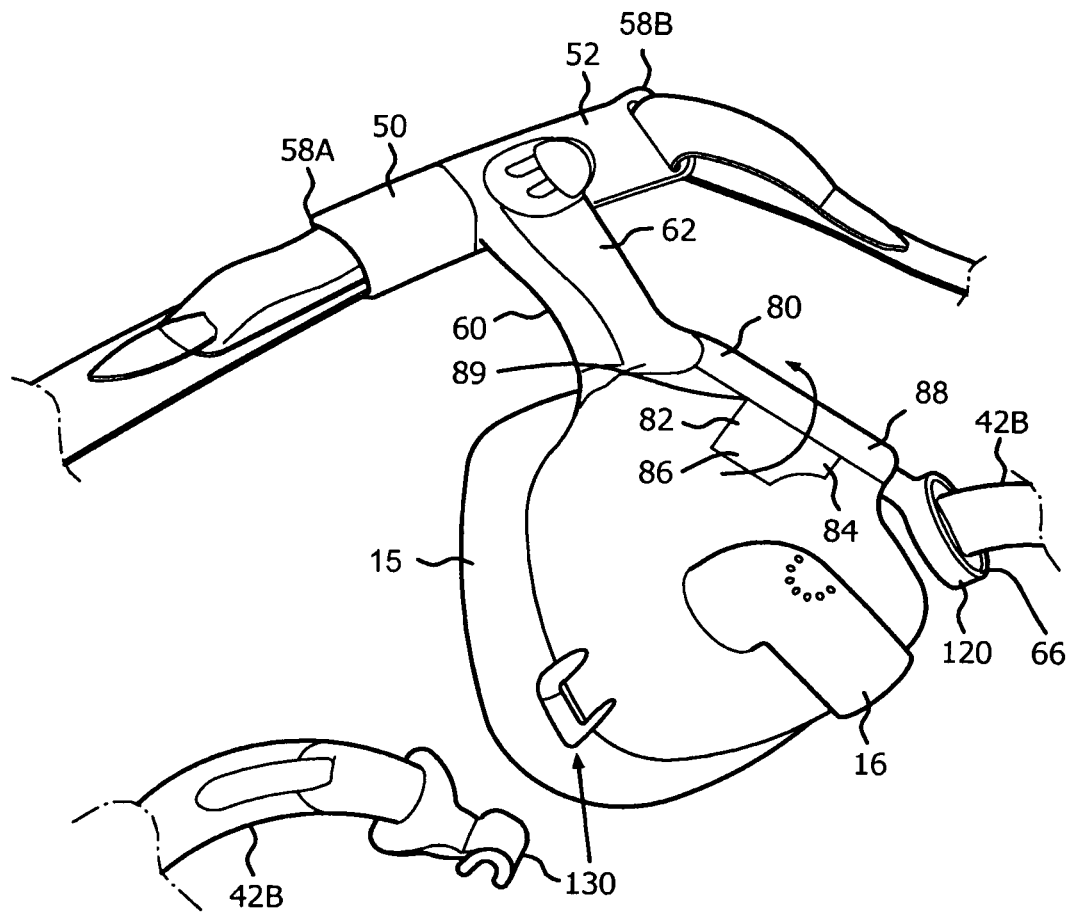
FIG. 2 is an isometric view of a patient interface device having an alternate hinge assembly.

As shown in FIG. 1, pivotable frame assembly hinge assembly 64 may be any type of hinge assembly. A hinge assembly includes at least a first component 80 that is coupled to a first element, and a second component 82 that is coupled to a second element. Hinge assembly first component 80 and hinge assembly second component 82 are pivotally coupled to each other. Therefore, first element and second element, i.e. the elements that hinge assembly first component 80 and hinge assembly second component 82 are coupled to, are also pivotally coupled to each other. Pivotable frame assembly hinge assembly 64 may be a barrel hinge 63 including a pin 90 and an elongated loop 92. That is, pin 90 is a rigid, elongated body 94 having a generally circular cross-section. Loop 92 is a tubular member having an elongated circular cavity. Loop 92 is coupled to, or unitary with, mask 10, and more specifically faceplate 12. Mask 10 is pivotally coupled to support assembly 40 when pin 90 is disposed in loop 92. That is, in this embodiment, hinge assembly 64 is coupled to both support assembly 40, and more specifically first support member 52, and mask 10. Therefore, mask 10 is pivotally coupled to support assembly 40. As shown in FIG. 2, pivotable frame assembly hinge assembly 64 is a living hinge 89 having a mounting element 86 and an elongated element 88. Further, mask 10 includes a mounting 84. Mounting element 86 and elongated element 88 are coupled by living hinge 89; thus, mounting element 86 and elongated element 88 are a hinge assembly first component 80 and hinge assembly second component 82. Mounting element 86 is coupled to, or fixed to mounting 84. Elongated element 88 may be an angled member 68, as discussed below.

Figure 3:
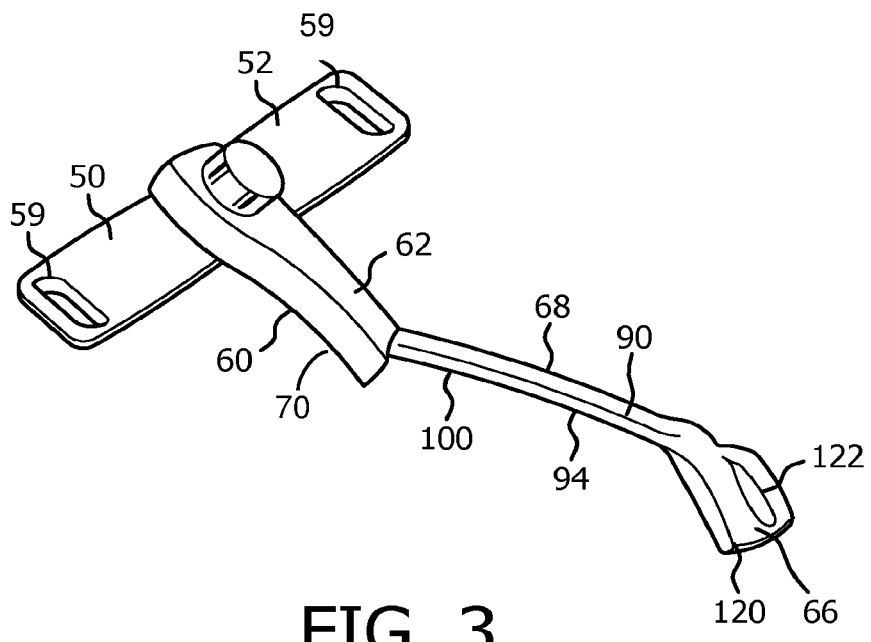
FIG. 3 is an isometric view of a portion of a pivotable frame assembly.

It is noted that, in this embodiment, shown in FIGS. 1 and 3, hinge assembly 64 includes both a vertical frame member 70 and an angled member 68. That is, pivotable frame assembly frame member 62 is a vertical frame member 70. Vertical frame member 70 is coupled to the support assembly first support member 52 as described above. Pin 90 (of hinge assembly 64) is an angled hinge member 100 extending downwardly at an angle from the vertical frame member 70 so that, when in use, the angled hinge member 100 is disposed over a user's cheek adjacent the user's nose. In this configuration, when pin 90 is disposed through mask loop 92, mask 10 may pivot from a first position, wherein the mask is pivoted away from the user's face, and a second position, wherein mask 10 is sealed against the user's face.

Figure 4:
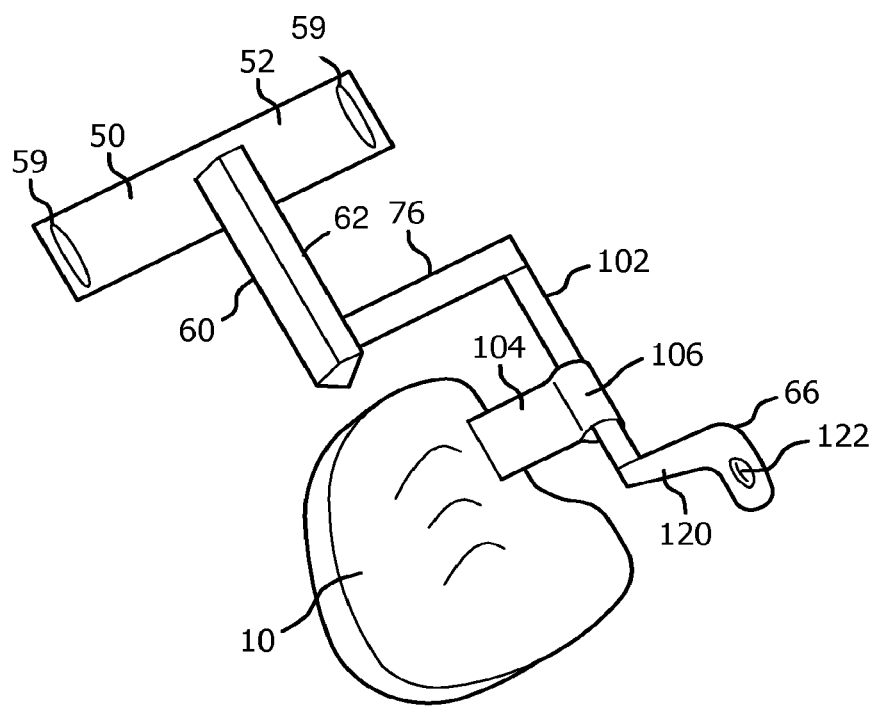
FIG. 4 is an isometric view of an alternate pivotable frame assembly.

In an alternate embodiment, shown in FIG. 4, pivotable frame assembly frame member 62 includes an elongated horizontal member 76 that is coupled to first support member 52 and is structured to extend generally horizontally under the user's eye when support assembly 40 is in use. In this embodiment, pin 90 (of hinge assembly 64) is a vertical hinge member 102 extending downwardly from the horizontal member 76 so that, when in use, the vertical hinge member 102 is disposed over a user's cheek and spaced from the user's nose.

The difference in the embodiments shown in FIGS. 1 and 4 is that in the embodiment shown in FIG. 1, mask 10 is disposed in front of a user's eye when mask 10 is in the first position. In the embodiment shown in FIG. 4, mask 10 pivots to the side of the user's eye. Further, in the embodiment shown in FIG. 4, mask 10 includes a stand-off member 104, as shown a generally flat plate 106, that allows loop 92 to be offset from faceplate 12.

Pivotable frame assembly strap coupling 66 is disposed at the distal end of hinge assembly 64, i.e. at the distal end of pin 90. Pivotable frame assembly strap coupling 66 includes a planar member 120 with a slot 122 therein. That is, pivotable frame assembly strap coupling 66 is a loop coupling, which is a semi-permanent coupling. One end of lower strap 42B is coupled to pivotable frame assembly strap coupling 66. The other end of lower strap 42B includes a temporary mask coupling 130, such as, but not limited to a snap, hook, (neither shown) or clip (as shown). Lower strap temporary mask coupling 130 is structured to be temporarily coupled to mask first, temporary, strap coupling 18 and corresponds to lower strap temporary mask coupling 130. That is, if lower strap temporary mask coupling 130 is a snap plug, then mask first, temporary, strap coupling 18 is a snap socket (neither shown).

As shown in FIG. 1, lower strap temporary mask coupling 130 is a hook-like clip and mask first, temporary, strap coupling 18 is a rod to which a hook-like clip may be attached. In this configuration, three of the four strap couplings 58A, 58B, 66 are semi-permanent couplings which are not directly coupled to mask 10. That is, three of the four strap couplings 58A, 58B, 66 are semi-permanent couplings which are coupled to the one of the frame assembly 50 or the pivotable frame assembly 60. Thus, mask 10 has a single strap coupling 18 whereby strap 42 may be directly coupled thereto. As used herein, a "mask having a single strap coupling whereby a strap may be directly coupled thereto" means that there is a single strap coupling 18 on mask 10; thus, while there may be other indirect strap couplings 18, there is only one coupling whereby strap 42 is directly coupled to mask 10. Moreover, mask strap coupling 18 is, as noted above, a temporary coupling.

Accordingly, when mask 10 is in the second position, lower strap temporary mask coupling 130 may be coupled to mask first, temporary, strap coupling 18. Lower strap 42B will maintain mask 10 in the second position. If a user needs to remove mask 10 briefly, i.e. to talk, the user does not have to remove the entire support assembly 40. That is, the user may simply decouple lower strap temporary coupling mask 130 from mask first, temporary, strap coupling 18 and move mask 10 to the first position. When the user needs to don mask 10 again, the user simply moves mask 10 to the second position and couples lower strap temporary mask coupling 130 to mask first, temporary, strap coupling 18 again. It is noted that upper strap 42A does not have to be loosened to move mask 10. Further, for the reasons noted above, even when removing support assembly 40 from the user's head, upper strap 42A does not have to be adjusted.

Further, hinge assembly 62 may include a biasing device 150. Biasing device 150 is structured to place mask 10 in a selected position and maintain mask 10 in that position until otherwise positioned. Biasing device 150 may be a torsion spring 152 disposed about pin 90 and biasing loop 92, or otherwise extend between hinge assembly first and second components 80, 82. Biasing device 150 is structured to bias mask 10 to be in either the first or second positions, noted above, or a neutral position somewhere between the first and second positions. When mask 10 is in the second position and lower strap temporary mask coupling 130 is coupled to mask first, temporary, strap coupling 18, the biasing device does not have sufficient force to lift mask 10 off the users face. Thus, any time mask 10 is in the second position, mask 10 creates a generally continuous seal with the user's face or a more complete seal with the user's face.

Figure 5:
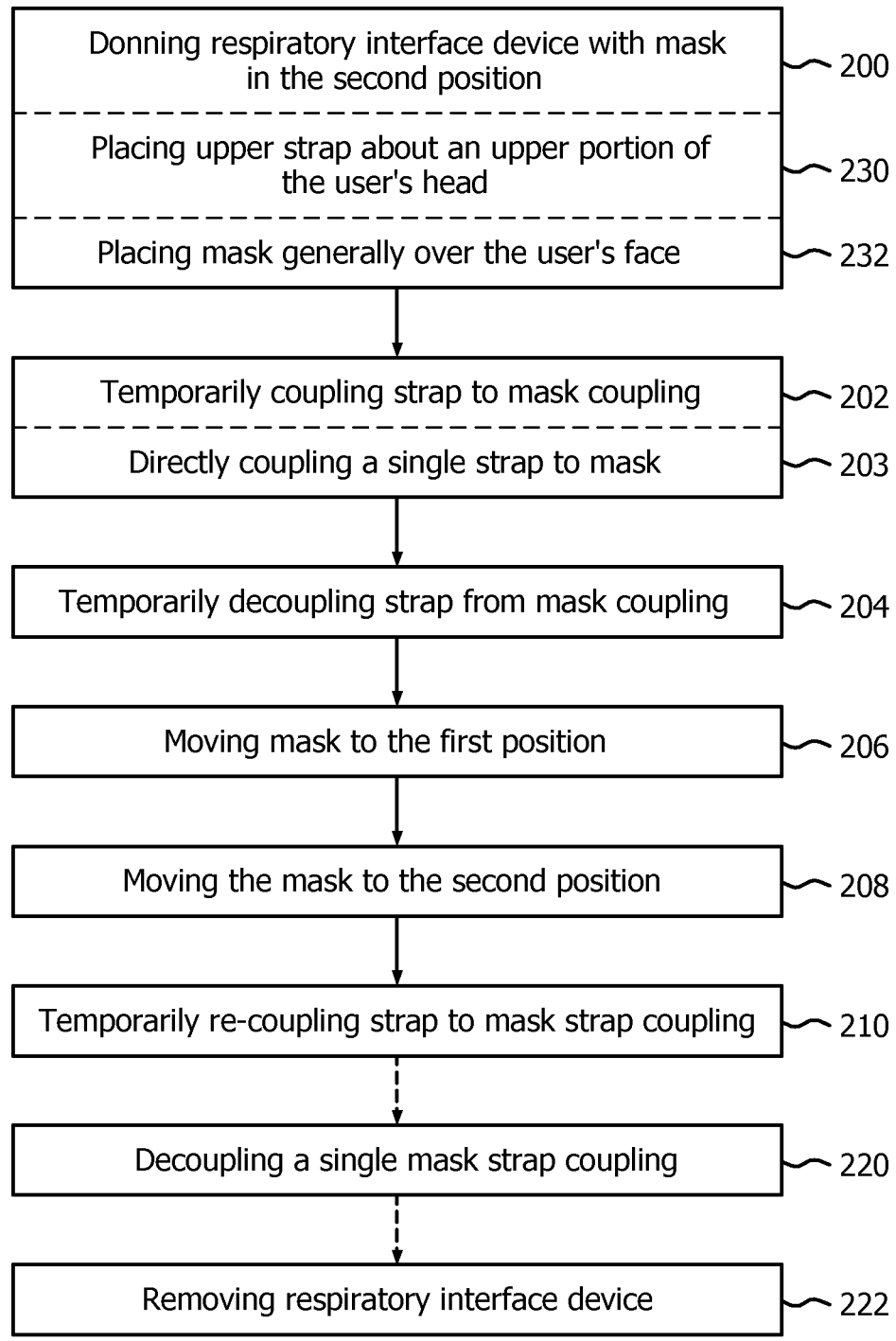
FIG. 5 is a flow chart of the steps for using the patient interface device.

As shown in FIG. 5, patient interface device 8 described above may be utilized by performing the method steps of donning 200 patient interface device 8 with mask 10 in the second position, temporarily coupling 202 strap 42B to mask strap coupling 18, temporarily decoupling 204 strap 42B from mask strap coupling 18, moving 206 mask 10 to the first position, moving 208 mask 10 to the second position, and temporarily re-coupling 210 strap 42B to mask strap coupling 18. It is understood that while mask 10 is in the second position following the donning of mask 10, the user may talk, eat, drink, etc. without mask 10 being in the way of the user's mouth.

As noted above, there is a single strap coupling 18 whereby strap 42B is directly coupled to mask 10 and this is the only coupling that must be decoupled in order to remove patient interface device 8. Thus, the method includes the further steps of decoupling 220 a single mask strap coupling 18, and, removing 222 patient interface device 8. That is, unlike other patient interface devices, wherein multiple strap couplings must be decoupled, or multiple straps must be loosened, prior to removal of the patient interface device, the present method allows for removal of patient interface device 8 by decoupling 220 a single mask strap coupling 18 without otherwise loosening straps 42. Further, the step of temporarily coupling 202 strap 42 to the mask strap coupling 18 includes the step of directly coupling 203 a single strap 42 to mask 10.

The step of donning 200 the patient interface device may include the steps of placing 230 upper strap 42A about an upper portion of the user's head, and, placing 232 mask 10 generally over the user's face. For the reasons set forth above, the step of donning 200 the patient interface device includes the step of coupling 234 a single temporary coupling between the mask and the support assembly. As noted above, upper strap 42A will be disposed above the user's ears. Further, in this configuration, lower strap 42B will be disposed below the user's ears. Thus, when lower strap 42B is coupled to mask 10, and pulled tight if required, patient interface device 8 may not easily be removed as the cross-sectional area defined by lower strap 42B and mask 10 is, typically, smaller than the cross-sectional area of the user's head.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A pivotable frame assembly for a patient interface device, the patient interface device including a mask and a support assembly, the mask having a first, temporary strap coupling, the support assembly including a first support member, a first upper strap and a second lower strap, the first strap semi-permanently coupled at two locations to the first support member, the second strap structured to be temporarily coupled to the mask first, temporary strap coupling, the pivotable frame assembly comprising:
   a frame member;
   a hinge assembly; and
   a strap coupling, wherein the frame member is elongated and structured to be coupled to the support assembly first support member and the frame member is structured to extend generally downward from the support assembly first support member at a location disposed over the user's nose, wherein the hinge assembly includes a first component and a second component, the hinge assembly first and second components being pivotally coupled to each other, the hinge assembly first component coupled to the frame member, the hinge assembly second component structured to be coupled to the mask, wherein, when the mask is coupled to the hinge assembly second component, wherein the hinge assembly second component is structured to selectively move the mask between a first position, wherein the mask is pivoted away from the user's face and is spaced from the user's face, and a second position, and wherein the mask is sealed against the user's face with a generally continuous seal.

2. The pivotable frame assembly of claim 1, wherein the strap coupling is structured to be semi-permanently coupled to the second strap.

3. The pivotable frame assembly of claim 1, wherein the hinge assembly includes one of a living hinge and a barrel hinge.

4. The pivotable frame assembly of claim 1, wherein:
   the frame member includes a horizontal member;
   the hinge assembly includes a vertical hinge member;
   the horizontal member coupled to the support assembly first support member, the frame member horizontal member extending laterally so that, when in use, the frame member horizontal member is disposed under one of a user's eye; and
   the vertical hinge member extending downwardly from the frame member horizontal member so that, when in use, the vertical hinge member is disposed over a user's cheek and spaced from the user's nose.

5. The pivotable frame assembly of claim 1, wherein the hinge assembly includes a biasing device, the biasing device structured to bias the mask to one of the first position, the second position, or a neutral position between the first and second positions.

6. A pivotable frame assembly for a patient interface device, the patient interface device including a mask and a support assembly, the mask having a first, temporary strap coupling, the support assembly including a first support member, a first upper strap and a second lower strap, the first strap semi-permanently coupled at two locations to the first support member, the second strap structured to be temporarily coupled to the mask first, temporary strap coupling, the pivotable frame assembly comprising:
   a frame member;
   a hinge assembly;
   a strap coupling, wherein the frame member is elongated and structured to be coupled to the support assembly first support member and the frame member is structured to extend generally downward from the support assembly first support member at a location disposed over the user's nose, wherein the hinge assembly includes a first component and a second component, the hinge assembly first and second components being pivotally coupled to each other, the hinge assembly first component coupled to the frame member, the hinge assembly second component structured to be coupled to the mask, wherein, when the mask is coupled to the hinge assembly second component, wherein the hinge assembly second component is structured to selectively move the mask between a first position, wherein the mask is pivoted away from the user's face and is spaced from the user's face, and a second position, and wherein the mask is sealed against the user's face with a generally continuous seal; and wherein the frame member includes a vertical member and the hinge assembly includes an angled member; the frame member vertical member coupled to the support assembly first support member; and the hinge assembly angled member extending downwardly at an angle from the frame member vertical member so that, when in use, the hinge assembly angled member is disposed over a user's cheek adjacent a user's nose.

7. A patient interface device comprising:
a mask having a first, temporary strap coupling;
a support assembly having a pivotable frame assembly, a frame assembly, and a strap assembly;
the strap assembly having at least one strap, the at least one strap having four mask couplings;
the frame assembly having a first support member structured to be coupled to a user's face, the first support member having two strap couplings;
the pivotable frame assembly including a frame member, a hinge assembly and a strap coupling;
the pivotable frame assembly frame member coupled to the support assembly first support member;
the hinge assembly having a first component and a second component, the hinge assembly first and second components being pivotally coupled to each other, the hinge assembly first component coupled to the frame member, the hinge assembly second component structured to be coupled to the mask; and
wherein, when the mask is coupled to the hinge assembly second component, the mask is structured to selectively move between a first position, wherein the mask is pivoted away from the user's face and is spaced from the user's face, and a second position, wherein the mask is structured to be sealed against the user's face with a generally continuous seal.

8. The patient interface device of claim 7, wherein the pivotable frame assembly strap coupling is structured to be semi-permanently coupled to the second strap.

9. The patient interface device of claim 7, wherein the pivotable frame assembly hinge assembly includes one of a living hinge and a barrel hinge.

10. The patient interface device of claim 7, wherein:
the frame member includes a horizontal member;
the hinge assembly includes vertical hinge member;
the horizontal member coupled to the support assembly first support member, the frame member horizontal member extending laterally so that, when in use, the frame member horizontal member is disposed under one of a user's eye; and
the vertical hinge member extending downwardly from the frame member horizontal member so that, when in use, the vertical hinge member is disposed over a user's cheek and spaced from the user's nose.

11. The patient interface device of claim 7, wherein the hinge assembly includes a biasing device, the biasing device structured to bias the mask to one of the first position, the second position, or a neutral position between the first and second positions.

12. The patient interface device of claim 7, wherein the mask has a single strap coupling whereby a strap is selectively directly coupled thereto, the mask strap coupling being a temporary coupling.

13. The patient interface device of claim 7, wherein three of the four strap couplings are semi-permanently coupled to one of the frame assembly or the pivotable frame assembly.

14. A patient interface device comprising:
a mask having a first, temporary strap coupling;
a support assembly having a pivotable frame assembly, a frame assembly, and a strap assembly;
the strap assembly having at least one strap, the at least one strap having four mask couplings;
the frame assembly having a first support member structured to be coupled to a user's face, the first support member having two strap couplings;
the pivotable frame assembly including a frame member, a hinge assembly and a strap coupling;
the pivotable frame assembly frame member coupled to the support assembly first support member;
the hinge assembly having a first component and a second component, the hinge assembly first and second components being pivotally coupled to each other, the hinge assembly first component coupled to the frame member, the hinge assembly second component structured to be coupled to the mask;
wherein, when the mask is coupled to the hinge assembly second component, the mask is structured to selectively move between a first position, wherein the mask is pivoted away from the user's face and is spaced from the user's face, and a second position, wherein the mask is structured to be sealed against the user's face with a generally continuous seal;
the pivotable frame assembly frame member includes a vertical member and the hinge assembly includes an angled member;
the pivotable frame assembly frame member vertical member coupled to the support assembly first support member; and
the hinge assembly angled member extending downwardly at an angle from the frame member vertical member so that, when in use, the hinge assembly angled member is disposed over a user's cheek adjacent a user's nose.

15. A method of using a patient interface device including a mask and a support assembly, the mask having a first, temporary strap coupling, the support assembly having a pivotable frame assembly, a frame assembly, and a strap assembly, the strap assembly having an upper strap and a lower strap, each strap having two mask couplings, the frame assembly having a first support member structured to be coupled to a user's face, the first support member having two strap couplings, the pivotable frame assembly including a frame member, a hinge assembly and a strap coupling, the pivotable frame assembly frame member coupled to the support assembly first support member, the hinge assembly having a first component and a second component, the hinge assembly first and second components being pivotally coupled to each other, the hinge assembly first component coupled to the frame member, the hinge assembly second component structured to be coupled to the mask, wherein, when the mask is coupled to the hinge assembly second component, the mask selectively moves between a first position, wherein the mask is pivoted away from the user's face, and a second position, wherein the mask is structured to be sealed against the user's face with a generally continuous seal, wherein one lower strap mask coupling is coupled to the pivotable frame assembly strap coupling, the method comprising the steps of:
donning the patient interface device with the mask in the second position;

temporarily coupling one of the upper strap or lower strap to the mask strap coupling;

temporarily decoupling one of the upper strap or lower strap to the mask strap coupling;

moving the mask to the first position wherein the mask is spaced from the user's face;

moving the mask to the second position; and temporarily re-coupling one of the upper strap or lower strap to the mask strap coupling.

16. The method of claim 15, wherein the step of donning the patient interface device includes the steps of:

placing the upper strap about an upper portion of the user's head; and placing the mask generally over the user's face.

17. The method of claim 15, wherein the step of temporarily coupling one of the upper strap or lower strap to the mask strap coupling includes the step of directly coupling a single strap to the mask.

18. The method of claim 15, wherein the step of donning the patient interface device includes the step of coupling a single temporary coupling between the mask and the support assembly.

19. The method of claim 15, further comprising the steps of:

decoupling a single mask strap coupling; and removing the patient interface device.

* * * * *